United States Patent [19]

Kennis

[11] 4,181,802

[45] Jan. 1, 1980

[54] 1-(HETEROCYCLYLALKYL)-1,3-DIHYDRO-2-H-BENZIMIDAZOLE-2-ONES

[75] Inventor: Ludo Kennis, Vosselaar, Belgium

[73] Assignee: Janssen Pharmaceutica N.V., Beerse, Belgium

[21] Appl. No.: 969,513

[22] Filed: Dec. 14, 1978

Related U.S. Application Data

[63] Continuation-in-part of Ser. No. 904,845, May 11, 1978, abandoned.

[51] Int. Cl.$^2$ ............... C07D 405/14; C07D 401/06; C07D 403/06
[52] U.S. Cl. ............................... 546/199; 260/326.34; 260/326.5 S; 260/326.5 CA; 260/342.3; 260/348.43; 260/348.44; 260/348.45; 260/348.46; 260/348.58; 424/267; 424/273 R; 546/271; 546/329; 546/338; 548/305

[58] Field of Search ................ 546/199; 260/326.34, 260/326.5 S, 326.5 CA

[56] References Cited

U.S. PATENT DOCUMENTS

| | | | |
|---|---|---|---|
| 3,818,017 | 6/1974 | Janssen et al. | 546/199 |
| 3,894,030 | 7/1975 | Janssen et al. | 546/199 |
| 3,910,930 | 10/1975 | Janssen et al. | 546/199 |

Primary Examiner—Alan L. Rotman
Assistant Examiner—Richard A. Schwartz
Attorney, Agent, or Firm—Salvatore R. Conte

[57] ABSTRACT

Novel 1-(heterocyclylalkyl)-1,3-dihydro-2H-benzimidazol-2-ones, wherein said heterocyclyl group is a 3-pyrrolidinyl or 3-piperidinyl group, each substituted in the 1-position with a 3-aryloxy-2-hydroxypropyl, 3-arylthio-2-hydroxypropyl or 2-(2,3-dihydro-1,4-benzodioxin-2-yl)-2-hydroxyethyl group, said compounds having useful β-adrenergic receptor blocking activity.

8 Claims, No Drawings

1-(HETEROCYCLYLALKYL)-1,3-DIHYDRO-2-H-BENZIMIDAZOLE-2-ONES

CROSS-REFERENCE TO RELATED APPLICATIONS

This is a continuation-in-part of our copending application Ser. No. 904,845, filed May 11, 1978, now abandoned.

BACKGROUND OF THE INVENTION

In U.S. Pat. Nos. 3,818,017 and 3,910,930 there are described a number of respectively 1-[1-(3-aryloxy-2-hydroxypropyl)-4-piperidinyl]-1,3-dihydro-2H-benzimidazol-2-ones and 1-{1-[2-(2,3-dihydro-1,4-benzodioxin-2-yl)-2-hydroxyethyl]-4-piperidinyl}-1,3-dihydro-2H-benzimidazol-2-ones, said compounds having antihypertensive properties, while in U.S. Pat. No. 4,035,369 there are described a number of 1-benzazolylalkyl-4-substituted-piperidines displaying neuroleptic activities. The compounds of this invention differ therefrom essentially by the manner in which the piperidinyl group or pyrrolidinyl group is connected with the 1,3-dihydro-2H-benzimidazol-2-one group, namely through the intermediate of a methylene bridge attached to the 3-position of said piperidine or pyrrolidone group.

DESCRIPTION OF THE PREFERRED EMBODIMENTS

This invention is concerned with a novel series of pharmacologically active compounds, more particularly 1-(heterocyclylalkyl)-1,3-dihydro-2H-benzimidazol-2-ones, which may be represented by the formula:

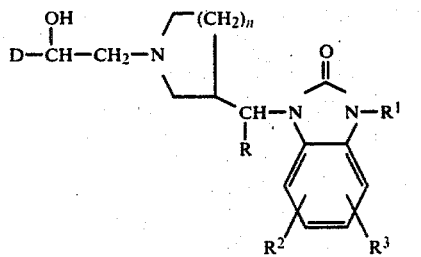

and the therapeutically acceptable acid addition salts thereof, wherein:

D is a member selected from the group consisting of the radicals

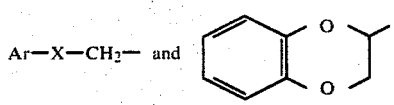

wherein X is selected from the group consisting of O and S and Ar is selected from the group consisting of phenyl, substituted phenyl, naphthalenyl and 2,3-dihydro-1H-indenyl, wherein substituted phenyl is phenyl having from 1 to 3 substituents each independently selected from the group consisting of halo, lower alkyl, lower alkenyl, lower alkynyl, lower alkyloxy, lower alkenyloxy, lower alkynyloxy, lower alkyloxy-lower alkyloxy, phenyl, cyano, lower alkanoyl, benzoyl, nitro, amino, lower alkanoylamino, mono- and di(lower alkyl)amino, aminocarbonylamino, phenylaminocarbonylamino, mono- and di(lower alkyl)aminocarbonylamino, lower alkylthio, phenyllower alkyl, 3-phenyl-2-propen-1-yloxy, aminocarbonyllower alkyl, mono- and di(lower alkyl)aminocarbonyllower alkyl and lower alkyloxycarbonyllower alkyl, provided that when more than 1 substituent is present only one thereof may be selected from the group consisting of phenyl, phenyllower alkyl, benzoyl, aminocarbonylamino, phenylaminocarbonylamino, mono- and di(lower alkyl)aminocarbonylamino, aminocarbonyllower alkyl, mono- and di(lower alkyl)aminocarbonyllower alkyl, lower alkyloxycarbonyllower alkyl, amino, nitro and cyano;

R is selected from the group consisting of hydrogen and lower alkyl;

n is the integer 1 or 2, provided that when said R is lower alkyl then said n is 2;

$R^1$ is a member selected from the group consisting of hydrogen, lower alkyl, lower alkenyl, lower alkyloxy-lower alkyl, phenoxylower alkyl, lower alkylcarbonyl-lower alkyl, cyano-lower alkyl, phenyl-lower alkyl, hydroxy-lower alkyl, di(lower alkyl)amino-lower alkyl, cyclic lower alkyleneamino-lower alkyl such as 1-pyrrolidinyl-lower alkyl and 1-piperidinyl-lower alkyl and lower alkyloxycarbonyl-lower alkyl; and $R^2$ and $R^3$ are each independently selected from the group consisting of hydrogen, halo, lower alkyl, lower alkyloxy and trifluoromethyl.

As used in the foregoing and following definitions, the term "halo" is generic to fluoro, chloro, bromo and iodo; "lower alkyl" is meant to include straight and branched hydrocarbon radicals having from 1 to 6 carbon atoms, such as, for example, methyl, ethyl, 1-methylethyl, 1,1-dimethylethyl, propyl, 1-methylpropyl, 2-methylpropyl, butyl, pentyl, hexyl and the like; "lower alkenyl" and "lower alkynyl" are meant to include straight and branched alkenyl, respectively alkynyl, radicals having from 2 to 4 carbon atoms, such as, for example, ethenyl, 2-propenyl, 2-butenyl and the like, and respectively ethynyl, 2-propynyl, 2-butynyl and the like; and the term "cycloalkyl" designates cyclopropyl, cyclobutyl, cyclopentyl and cyclohexyl.

The compounds of formula (I) may generally be prepared by the reaction of an appropriate oxirane derivative of the formula (II) wherein D has the above-indicated meaning, with a cyclic amine of the formula (III), wherein n, R, $R^1$, $R^2$ and $R^3$ are as previously defined.

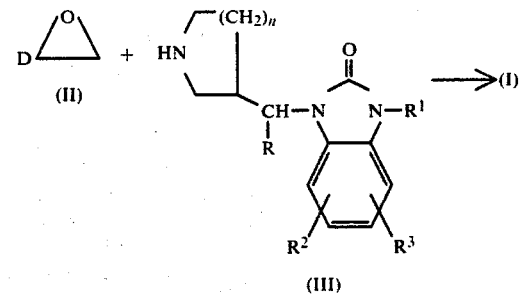

The reaction of (II) with (III) is conveniently conducted in a suitable reaction-inert organic solvent such as, for example, an alcohol, such as, for example, methanol, ethanol, 2-propanol and the like, or an aliphatic or alicyclic ketone, such as, for example, 2-propanone, 2-butanone, 4-methyl-2-pentanone, cyclohexanone and the like. The addition of an appropriate base, such as, for example, an alkali metal carbonate or hydrogen carbonate, may be utilized to enhance the rate of reaction. The reaction is preferably carried out at a somewhat elevated temperature and most preferably at the reflux temperature of the reaction mixture.

The compounds of formula (I) wherein $R^1$ is other than hydrogen, said $R^1$ being represented by $R^1_a$ and said compounds by the formula (I-a) may also be prepared starting from the corresponding compounds (I) wherein said $R^1$ is hydrogen, (I-b), by introducing into the latter the desired substituent $R^1_a$ according to methods, known in the art.

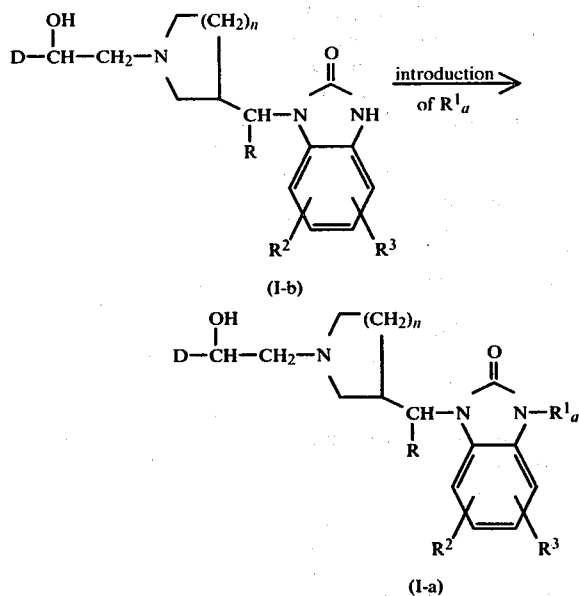

Depending on the nature of $R^1_a$ the following methods may, for example, be employed therefore.

In general the introduction of $R^1_a$ into (I-b) may be accomplished by the reaction of (I-b) with an appropriate reactive ester of the formula $R^1_a$-X, wherein $R^1_a$ is as previously defined and X is an appropriate reactive ester group such as, for example, chloro, bromo, iodo or a sulfonyloxy group, such as, for example, methylsulfonyloxy or 4-methylphenylsulfonyloxy.

When $R^1_a$ represents a lower alkylcarbonyl-ethyl, a cyanoethyl or a lower alkyloxycarbonyl-ethyl group, said group may be introduced by the reaction of (I-b) with an appropriate reactive alkene, such as, for example, 2-propenenitrile, a lower alkyl propenoate or an α-β unsaturated ketone.

The compounds of formula (I) wherein D represents a radical Ar—X—CH₂— wherein Ar is phenyl, substituted with an aminocarbonyllower alkyl radical or a mono- or di(lower alkyl)aminocarbonyllower alkyl radical, may be prepared starting from the corresponding lower alkyloxycarbonyl lower alkyl-substituted compounds by reacting the latter with ammonia or with an appropriate primary or secondary amine in a suitable solvent such as, for example, an alcohol, e.g. methanol, ethanol and the like.

The starting materials of formula (II) herein are generally known and they may be prepared following art-known procedures as described in the literature for the preparation of such known or similar compounds.

Starting materials of formula (II) wherein D represents a radical of the formula Ar—X—CH₂—, (II-a), can generally be prepared by the reaction of an appropriate sodium phenolate or thiolate of the formula (IV) with an appropriate 2-(halomethyl)oxirane of formula (V), preferably a 2-(chloromethyl)oxirane. The sodium salts of formula (IV) are conveniently derived from the corresponding phenols or thiols by treating the latter with an appropriate strong base such as sodium methanolate in methanol or sodium hydride in N,N-dimethylformamide.

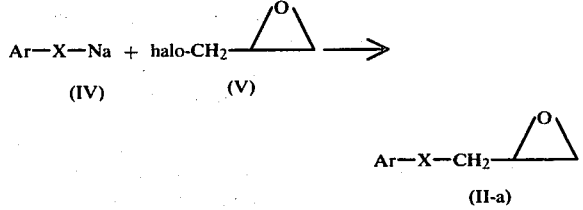

The starting material of formula (II) wherein D represents a 2,3-dihydro-1,4-benzodioxin-2-yl radical is described e.g. in U.S. Pat. No. 3,910,930.

The starting materials of formula (III), wherein R, $R^1$, $R^2$ and $R^3$ are as previously defined and n is the integer 2, (III-a), can conveniently be derived from an appropriate pyridine derivative of formula (VI) by catalytically hydrogenating the latter in the presence of an appropriate catalyst such as rhodium-on-aluminium-oxide, rhodium-on-charcoal or palladium-on-charcoal, in an appropriate polar solvent such as, for example, methanol or acetic acid.

When $R^2$ and/or $R^3$ represents a halogen atom said atom may in certain circumstances be eliminated during the catalytic hydrogenation step, particularly when palladium-on-charcoal is used as a catalyst.

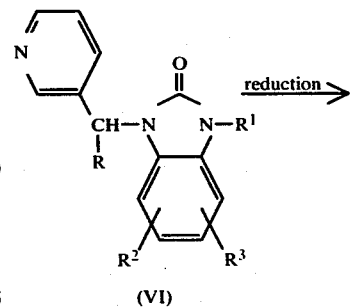

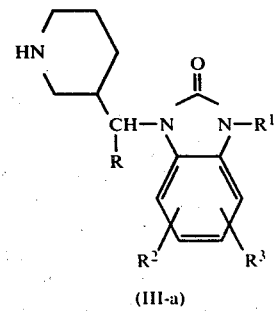

Intermediates of formula (VI) wherein $R^1$ is hydrogen, (VI-a), can generally be obtained by the following procedures.

An appropriate precursor of formula (VII-a), wherein R has the previously indicated meaning, is reacted with an appropriate 2-halonitrobenzene of formula (VIII), wherein $R^2$ and $R^3$ are as previously defined, according to art-known procedures. The thus obtained intermediate of formula (IX) is then subjected to a nitro-to-amine reduction, e.g. by catalytically hydrogenating (IX) in the presence of an appropriate catalyst such as, for example, Raney-nickel or platinum-on-charcoal, in a relatively polar solvent such as, for example, a lower alkanol, e.g. methanol or ethanol, preferably in the presence of a small amount of a catalyst-poison such as thiophene, yielding an intermediate of formula (X). The latter is then cyclized to obtain the corresponding 1,3-dihydro-2H-benzimidazol-2-one of formula (VI-a). Said cyclization reaction may be carried out in an art-known manner, e.g. by stirring and heating (X) with urea.

The intermediates of formula (VI-a) may alternatively be prepared by reacting a 1,3-dihydro-1-(1-methylethenyl)-2H-benzimidazol-2-one of formula (XI), wherein $R^2$ and $R^3$ are as previously defined, with an appropriate pyridine derivative of formula (VII-b), wherein R is as previously defined and X is an appropriate reactive ester group such as, for example, halo, particularly chloro, bromo or iodo, or a sulfonyloxy group such as methylsulfonyloxy or 4-methylphenylsulfonyloxy, following art-known procedures, to obtain an intermediate of formula (XII). Elimination of the 1-methylethenyl group of the latter compound by acid hydrolysis yields the desired intermediates of formula (VI-a).

The foregoing reactions are illustrated in the following schematic representation.

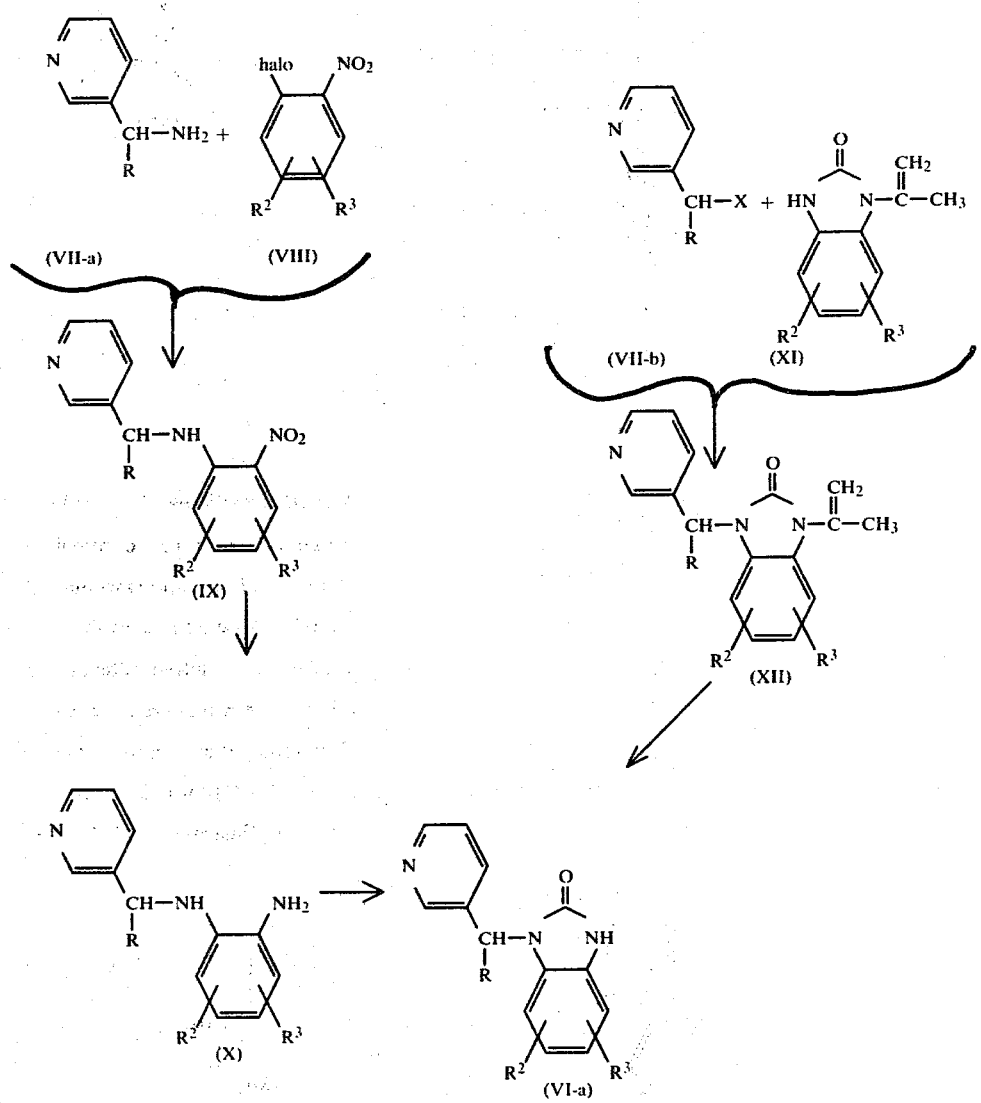

The intermediates of formula (VI) wherein $R^1$ is other than hydrogen, i.e. intermediates of formula (VI-b) wherein $R^1_a$ has the previously indicated meaning, can be prepared starting from the corresponding (VI-a) by introducing into the latter the desired $R^1_a$ group following the same procedures as previously described herein for the preparation of the compounds (I-a) starting from (I-b).

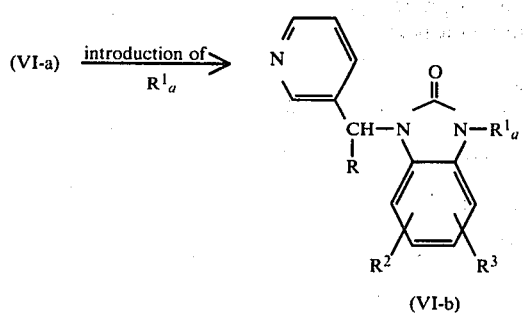

The intermediates of formula (VI-b) can alternatively be prepared starting from a 1,3-dihydro-1-(1-methylethenyl)-2H-benzimidazol-2-one of formula (XI) wherein $R^2$ and $R^3$ are as previously defined, by the steps of:

(i) introducing into said (XI) a radical $R^1_a$ according to the procedures previously described herein;
(ii) eliminating the 1-methylethenyl group of the thus obtained intermediate (XIII) by acid hydrolysis; and
(iii) reacting the thus obtained intermediate of formula (XIV) with an appropriate pyridine derivative of formula (VII-b) following art-known procedures.

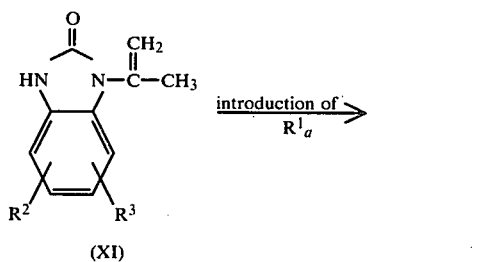

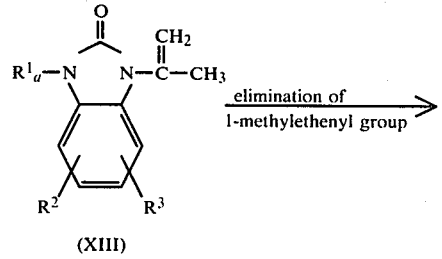

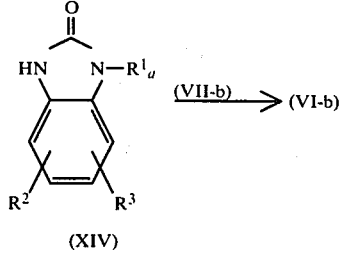

The starting materials of formula (III), including those wherein n is 1, can also be derived from a compound of formula (XV), wherein $R^4$ represents an appropriate protecting group, such as, for example, a phenylmethyl radical, by eliminating said protecting group according to art-known procedures. When $R^4$ represents a phenylmethyl group, said group is easily removed by catalytic hydrogenation in the presence of an appropriate catalyst such as, for example, palladium-on-charcoal, in a relatively polar organic solvent such as, for example, methanol.

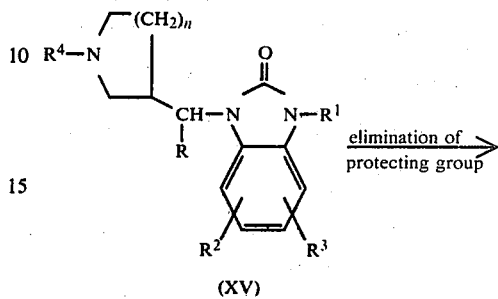

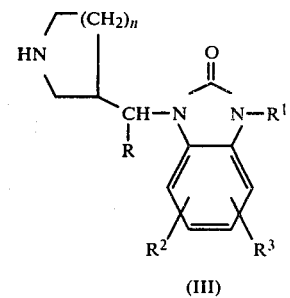

The intermediates of formula (XV) wherein $R^1$ is hydrogen, (XV-a), can conveniently be prepared by the reaction of an appropriate 1,3-dihydro-1-(1-methylethenyl)-2H-benzimidazol-2-one of formula (XI) with an appropriate reactive ester of formula (XVI) wherein R, $R^4$, n and X are as previously defined, and, subsequently eliminating the 1-methylethenyl group of the thus obtained (XVII) by acid hydrolysis. The foregoing reactions are illustrated as follows:

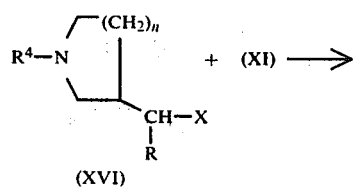

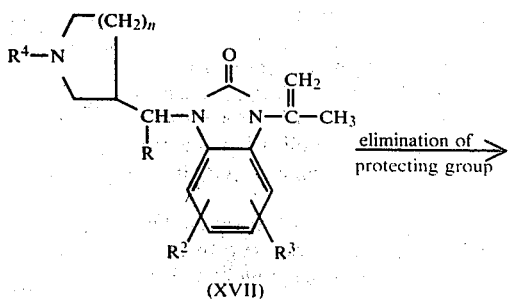

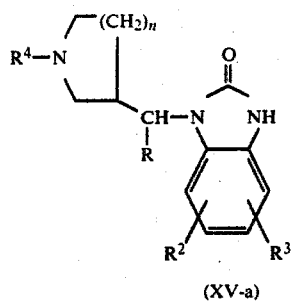

(XV-a)

Intermediates of formula (XV) wherein $R^1$ is other than hydrogen, i.e. intermediates of formula (XV-b), wherein $R^1_a$ is as previously defined, can conveniently be prepared by the reaction of an appropriate reactive ester of formula (XVI) with an appropriate 1,3-dihydro-2H-benzimidazol-2-one of formula (XIV) following standard N-alkylating procedures as previously described herein.

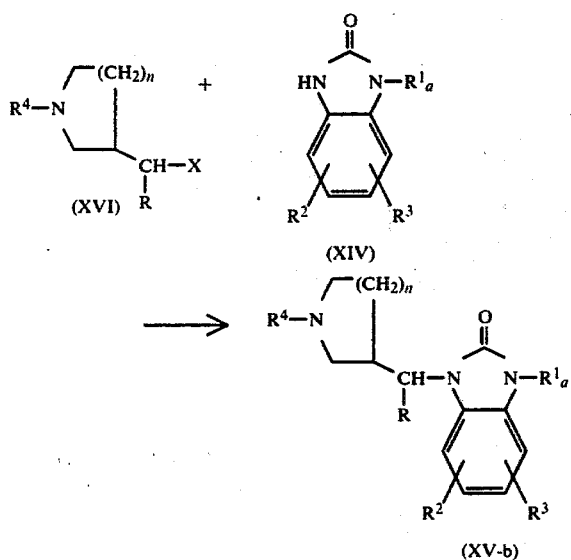

The intermediates of formula (XV-b) can alternatively be prepared by introducing the desired $R^1_a$-group into an intermediate of formula (XV-a) following art-known procedures as previously described herein.

The starting materials of formula (VII-a) can easily be prepared by methods known to those skilled in the art, such as the following.

The starting material of formula (VII-a) wherein R is hydrogen, i.e. 3-pyridinemethanamine, (VII-a-1), is a known compound that may easily be prepared by the reduction of 3-cyanopyridine. The starting materials of formula (VII-a) wherein R represents a lower alkyl radical, (VII-a-2), can conveniently be prepared by subjecting 3-cyanopyridine, (XVIII), to a Grignard reaction with an appropriate alkyl magnesium halide R—Mg—Y wherein Y represents chloro, bromo or iodo, preferably the bromide, to obtain a ketone of formula (XIX). The latter is then reacted with hydroxylamine to obtain an oxime of formula (XX) which in turn is reduced to obtain the desired amine of formula (VII-a-2). The latter reduction can conveniently be carried out by hydrogenating (XX) in the presence of an appropriate catalyst such as, for example, palladium-on-charcoal. The foregoing reactions may be illustrated as follows.

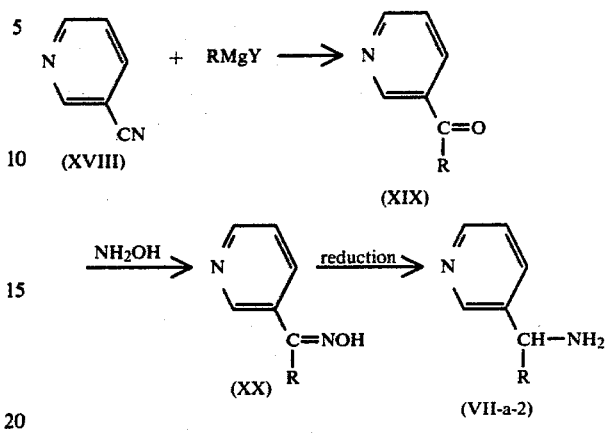

The starting materials of formula (VII-b) can conveniently be obtained by the reduction of the carbonyl group of an appropriate 3-(lower alkylcarbonyl) pyridine of formula (XIX) and subsequent transformation of thus obtained alcohol (XXI) into a reactive ester group such as, for example, halo, particularly chloro, bromo or iodo, or a sulfonyloxy group, such as, for example, methylsulfonyloxy or 4-methylphenylsulfonyloxy, following art-known procedures. Chlorides and bromides may be prepared by the reacton of (XXI) with an appropriate halogenating agent such as, for example, thionyl chloride, phosphoryl chloride, phosphor pentachloride, phosphor pentabromide and the like. Iodides are preferably derived from the corresponding chlorides or bromides by replacement of the chlorine or bromine atom thereof with iodine. Methanesulfonates and 4-methylbenzenesulfonates are easily obtained by the reaction of (XXI) with respectively methanesulfonyl chloride or 4-methylbenzenesulfonyl chloride.

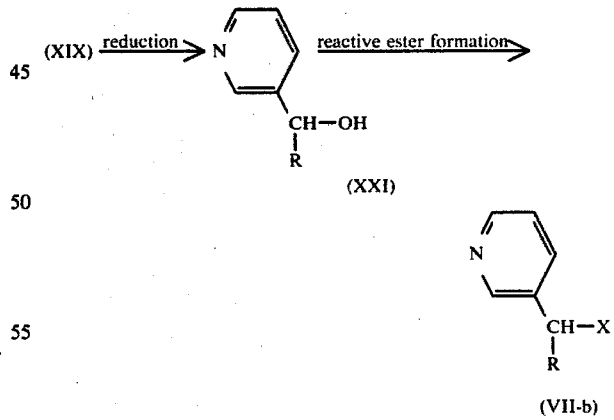

Starting materials of formula (XVI) wherein R, $R^4$ and X are as previously defined and n is 2, (XVI-a), can easily be obtained by reducing the pyridine group of an appropriate reactive ester of formula (VII-b) according to art-known procedures as previously described herein, to obtain a piperidine derivative of formula (XXII), and subsequently introducing into the latter the desired protecting group $R^4$ by the application of standard methodologies, such as, for example, by the reaction of (XXII) with chloromethylbenzene or phenylmethyl methanesulfonate.

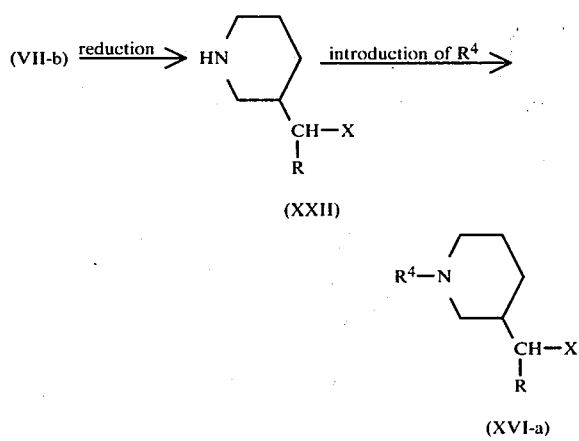

Reactive esters of formula (XVI) wherein n is 1 can be prepared following the procedures described in U.S. Pat. No. 2,826,588.

The starting materials of formulae (VII) and (XI) are generally known and they may all be prepared according to methodologies known in the art.

As a result of their basic properties, the compounds of formula (I) can be converted to their therapeutically active, non-toxic acid addition salt form by treatment with an appropriate acid, such as, for example, an inorganic acid, such as hydrohalic acid, e.g., hydrochloric, hydrobromic, and the like, and sulfuric acid, nitric acid, phosphoric acid and the like; or an organic acid, such as, for example, acetic, propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, α-hydroxybenzoic, 4-amino-2-hydroxybenzoic and the like acids. Conversely, the salt form can be converted by treatment with alkali into the free base form. It is obvious from formula (I) that the compounds of this invention have at least two asymmetric carbon atoms within their structure, more particularly the carbon atom whereto the hydroxy group is attached and the carbon atom of the piperidine group or the pyrrolidine group whereto the methylene bridge is attached, and consequently they may exist under different stereochemically isomeric forms. When D represents a 2,3-dihydro-1,4-benzodioxin-2-yl radical an additional asymmetric carbon atom is present and the compounds may possess the erythro and threo configuration. It is obvious that when R is different from hydrogen another additional asymmetric carbon atom is present; this provides a second possibility for the compounds to take an erythro or threo configuration. Pure isomeric forms of the compound (I) may be obtained by the application of art-known procedures. Diastereoisomers may be separated by physical separation methods such as selective crystallization and chromatographic techniques, such as, for example, counter current distribution, and enantiomers may be separated from each other by the selective crystallization of their diastereomeric salts with optically active acids, or of their diastereomeric esters of the secondary alcohol with an optically active acid. Pure isomeric forms may also be derived from the corresponding forms of the appropriate starting materials, provided that the stereochemistry of the concerned groups is not altered during the reactions. Isomers of compounds of formula (I) are naturally intended to be embraced within the scope of this invention.

The compounds of formula (I) and their pharmaceutically acceptable acid addition salts and stereochemically isomeric forms possess strong β-adrenergic receptor blocking activity and as such they can be used in the treatment and prevention of disorders of the coronary vascular system. The useful β-adrenergic receptor blocking activities of the compounds (I) were demonstrated in vitro using the Guinea-pig right atrium test and the Guinea-pig tracheal ring test which are described hereafter.

1. GUINEA-PIG RIGHT ATRIUM ($\beta_1$)

Spontaneously beating right atria are dissected from guinea-pigs (400±50 g). A triangular strip of atrium, including the sinoatrial node is excised together with the anterior vena cava.

The vena is fixed to a glass muscle holder and the opposite atrial muscle is connected to a Grass isometric transducer. Atria are suspended at optimal preload in a 100 ml Krebs-Henseleit solution, containing 2 g/l glucose, at 37.5° C. and aerated with 95% $O_2$ and 5% $CO_2$.

Heart rate and contractile force are recorded by means of a Grass FTO3C isometric transducer. Output signals amplified by an isometric transducer amplifier (J.S.I.) via a cardiotachometer (J.S.I.) are recorded on a Honeywell XYY' recorder. After a stabilization period of 45 min isoprenaline is infused in linearily increased doses for a period of 7 min. This produces a dose related increase in heart rate (a). After washing out isoprenaline a stabilization period of 15 min. is allowed. A drug is then added to the bath fluid for 30 min. During this incubation period possible direct chronotropic and inotropic effects of the drug are determined. Following this, a second dose-response curve for isoprenaline is produced by infusion during 10 minutes (b). The slope of the increase in rate is graphically estimated for each period of isoprenaline addition and the ratio b/a is calculated. Based on solvent experiments a ratio of less than 0.70 is considered as the criterion of inhibitory activity. $ED_{50}$-values are estimated graphically.

2. GUINEA-PIG TRACHEAL RING ($\beta_2$)

The trachea is dissected from guinea-pigs (400±50 g). Four rings, approximately 8 mm in width, are then cut from each trachea. Cartilaginous parts of the tracheal ring are mounted horizontally between two metal rods, one of which is attached to a glass organholder, the other rod being connected to a Grass isometric transducer. Using such a technique the tracheal smooth muscle is suspended optimally i.e. midway between the cartilaginous parts. the prepared rings are suspended in a 100 ml organ chamber filled with Tyrode solution, maintained at 35° C. and aerated with 95% $O_2$ and 5% $CO_2$. The preparation is maintained at tension of 1.5 g throughout the experiment. Tension changes recorded are thus an expression of contraction or relaxation. After a stabilization period of 30 min contraction is induced by adding methacholine (1 μg/ml) to the bath for a 10 min period. Addition of isoprenaline (0.08 μg/ml) for 4 min. in the presence of methacholine induces a relaxation of the tracheal ring. This procedure is repeated twice before adding the drug (t-33'; t-19') and once 30 min after addition of the drug. During the incubation period any direct effects of the drug are measured. A 50% inhibition of the agonist-induced response is used as the criterion of effectiveness and $ED_{50}$ values (with fiducial limits) are determined by probit analysis.

($\beta_1$) may be considered as an index of the cardioselectivity of the test drug.

Typical results obtained in the above experiments with a number of the compounds of formula (I) are given in the following tables I and II which are only intended to illustrate and not to limit the scope of the invention.

TABLE I $$Ar-O-CH_2-CH(OH)-CH_2-N\text{(piperidine-CH}_2\text{-N(benzimidazole-COCH}_3\text{)-NH)}-R^2$$

| Ar | $R^2$ | $\beta_1 = ED_{50}$ right atrium in mg/l | $\beta_2 = ED_{50}$ tracheal ring in mg/l | $\beta_2/\beta_1$ |
|---|---|---|---|---|
| $C_6H_5$ | H | 0.00063 | 0.0089 | 15 |
| 3-$(CH_3)$—$C_6H_4$ | H | 0.0025 | 0.02 | 8 |
| 2-$(C_2H_5)$—$C_6H_4$ | H | 0.0025 | 0.02 | 8 |
| 4-$(nC_3H_7)$—$C_6H_4$ | 5-F | 0.01 | 0.63 | 63 |
| 2,3-$(CH_3)_2$—$C_6H_3$ | H | 0.0025 | 0.02 | 8 |
| 2-$(CH_2=CH-CH_2)$—$C_6H_4$ | H | 0.0025 | 0.036 | 14 |
| 1-naphthalenyl | H | 0.01 | 1.25 | 125 |
| 2-$CN$—$C_6H_4$ | H | 0.0025 | 0.005 | 2 |
| 2-$CN$—$C_6H_4$ | 6-Cl | 0.005 | 0.08 | 16 |
| 1-naphthalenyl | 6-Cl | 0.005 | 0.16 | 32 |
| $C_6H_5$ | 5-F | 0.00125 | 0.005 | 4 |
| $C_6H_5$ | 5-Cl | 0.005 | 0.08 | 16 |
| 2-$(CH_3CO)$—$C_6H_4$ | H | 0.00125 | 0.00125 | 1 |
| 4-$(CH_3CO)$—$C_6H_4$ | H | 0.0025 | 0.02 | 8 |
| 2-$(CH_3O)$—$C_6H_4$ | H | 0.001 | 0.005 | 5 |
| 2-$(CH_3O)$—$C_6H_4$ | 6-Cl | 0.00063 | 0.04 | 63 |
| 4-$(CH_3O)$—$C_6H_4$ | H | 0.01 | 0.02 | 2 |
| 2-$(C_2H_5O)$—$C_6H_4$ | H | 0.0025 | 0.01 | 4 |
| 2-$(C_2H_5O)$—$C_6H_4$ | 6-Cl | 0.01 | 0.18 | 18 |
| 2-$(nC_3H_7O)$—$C_6H_4$ | H | 0.0025 | 0.01 | 4 |
| 2-$(CH_2=CH-CH_2O)$—$C_6H_4$ | H | 0.00125 | 0.02 | 16 |
| 2-$(iC_3H_7O)$—$C_6H_4$ | H | 0.005 | 0.04 | 8 |
| 4-$(CH_3S)$—$C_6H_4$ | H | 0.00063 | 0.02 | 32 |
| 4-$(CH_3CONH)$—$C_6H_4$ | H | 0.0025 | 0.18 | 72 |
| 4-$(nC_4H_9-NH-CO-NH)$—$C_6H_4$ | H | 0.01 | 0.08 | 8 |
| 4-Cl—$C_6H_4$ | H | 0.02 | 0.32 | 16 |
| 2-Br—$C_6H_4$ | H | 0.0025 | 0.055 | 22 |
| 4-Br—$C_6H_4$ | H | 0.005 | 1.25 | 250 |
| 4-F—$C_6H_4$ | 6-Cl | 0.005 | 0.08 | 16 |
| 4-F—$C_6H_4$ | H | 0.00125 | 0.01 | 8 |
| 4-F—$C_6H_4$ | 5-Cl | 0.005 | 0.31 | 62 |
| 3,5-$(CH_3)_2$-4-Cl—$C_6H_2$ | H | 0.0025 | 1.25 | 500 |

TABLE II

| Compound | $\beta_1 = ED_{50}$ right atrium in mg/l | $\beta_2 = ED_{50}$ tracheal ring in mg/l | $\beta_2/\beta_1$ |
|---|---|---|---|
| (benzodioxane-O-CH$_2$-CH(OH)-CH$_2$-N(piperidine-CH$_2$-N(benzimidazole-COCH$_3$)-NH)) | 0.005 | 0.02 | 4 |

The ratio of the $ED_{50}$-values obtained in respectively the tracheal ring test ($\beta_2$) and in the right atrium test The compounds of formula (I) and the pharmaceutically acceptable acid addition salts thereof can be formulated into compositions suitable for the usual routes of administration according to standard pharmaceutical formulation techniques.

The following examples are intended to further illustrate and not to limit the scope of the present invention. Unless otherwise stated all parts therein are by weight.

EXAMPLE I

A mixture of 65 parts of 3-pyridinemethanamine, 94 parts of 1-chloro-2-nitrobenzene, 80 parts of sodium carbonate and 800 parts of 1-butanol is stirred and refluxed over week-end. The reaction mixture is cooled, filtered and the filtrate is evaporated. The residue is purified by column-chromatography over silica gel using a mixture of trichloromethane and methanol (98:2 by volume) as eluent. The pure fractions are collected and the eluent is evaporated. The residue is crystallized from 2,2'-oxybispropane. The product is filtered off and dried, yielding 33 parts (23%) of N-(2-nitrophenyl)-3-pyridinemehtanamine.

A mixture of 33 parts of N-(2-nitrophenyl)-3-pyridine-methanamine and 480 parts of methanol is hydrogenated at normal pressure and at room temperature with 5 parts of Raney-nickel catalyst. After the calculated amount of hydrogen is taken up, the catalyst is filtered off and the filtrate is evaporated, yielding 33 parts of N-(3-pyridinylmethyl)-1,2-benzenediamine as a residue.

A mixture of 25 parts of N-(3-pyridinylmethyl)-1,2-benzenediamine and 11 parts of urea is melted together to 180°–190° C. and the melt is stirred for 30 minutes at this temperature. The reaction mixture is cooled and dissolved in a mixture of trichloromethane and methanol. The solvent is evaporated and the residue is crystallized from 4-methyl-2-pentanone. The product is filtered off and dried, yielding 24 parts (86%) of 1,3-dihydro-1-(3-pyridinylmethyl)-2H-benzimidazol-2-one; mp. 160.5° C.

A mixture of 21 parts of 1,3-dihydro-1-(3-pyridinylmethyl)-2H-benzimidazol-2-one and 400 parts of methanol is hydrogenated at normal pressure and at room temperature with 5 parts of a mixture of 0.25 parts of rhodium and 4.75 parts of aluminium oxide. After the calculated amount of hydrogen is taken up, the catalyst is filtered off and the filtrate is evaporated. The residue is converted into the hydrochloride salt in 4-methyl-2-pentanone and 2-propanol. The salt is filtered off and dried, yielding 20 parts (83.3%) of 1,3-dihydro-1-(3-piperidinylmethyl)-2H-benzimidazol-2-one monohydrochloride; mp. 273.5° C.

EXAMPLE II

Following the procedure of Example I and using equivalent amounts of the appropriate starting materials there are prepared:

6-chloro-1,3-dihydro-1-(3-piperidinylmethyl)-2H-benzimidazol-2-one;

5,6-dichloro-1,3-dihydro-1-(3-piperidinylmethyl)-2H-benzimidazol-2-one; mp. 240.9° C.;

5-fluoro-1,3-dihydro-1-(3-piperidinylmethyl)-2H-benzimidazol-2-one; and 5-chloro-1,3-dihydro-1-(3-piperidinylmethyl)-2H-benzimidazol-2-one.

EXAMPLE III

A mixture of 52.5 parts of α-methyl-3-pyridinemethanamine, 84.5 parts of 1,4-dichloro-2-nitrobenzene, 53 parts of sodium carbonate and 320 parts of 1-butanol is stirred and refluxed for 72 hours. The reaction mixture is evaporated and water is added to the residue. The oily product is extracted with methylbenzene. The extract is dried, filtered and evaporated. The residue is converted into the hydrochloride salt in 2,2'-oxybispropane, 4-methyl-2-pentanone and 2-propanol. The oily salt is separated and crystallized from 2-propanol, yielding 46 parts (34%) of N-(4-chloro-2-nitrophenyl)-α-methyl-3-pyridinemethanamine monohydrochloride.

A mixture of 46 parts of N-(4-chloro-2-nitrophenyl)-α-methyl-3-pyridinemethanamine monohydrochloride and 400 parts of methanol is hydrogenated at normal pressure and at room temperature with 5 parts of Raney-nickel catalyst. After the calculated amount of hydrogen is taken up, the catalyst is filtered off and the filtrate is evaporated, yielding 41.5 parts (100%) of 4-chloro-N$^1$-[1-(3-pyridinyl)ethyl]-1,2-benzenediamine monohydrochloride as a residue.

A mixture of 41.5 parts of 4-chloro-N$^1$-[1-(3-pyridinyl)ethyl]-1,2-benzenediamine monohydrochloride and 27 parts of urea is stirred and heated for 1.50 hours in an oil-bath at about 190° C. The reaction mixture is cooled, water and trichloromethane are added and the layers are separated. The organic phase is dried, filtered and evaporated. The residue is crystallized from a mixture of 4-methyl-2-pentanone and 2,2'-oxybispropane. The product is filtered off and dried, yielding 26 parts (63.5%) of 5-chloro-1,3-dihydro-1-[1-(3-pyridinyl)ethyl]-2H-benzimidazol-2-one; mp. 190° C.

A mixture of 24 parts of 5-chloro-1,3-dihydro-1-[1-(3-pyridinyl)ethyl]-2H-benzimidazol-2-one, 10 parts of sodium acetate and 400 parts of acetic acid is hydrogenated at normal pressure and at a temperature of 60° C. with 2 parts of palladium-on-charcoal catalyst 10%. After the calculated amount of hydrogen is taken up, the catalyst is filtered off and the filtrate is evaporated. The residue is taken up in water and the whole is alkalized with concentrated ammonium hydroxide. The product is extracted three times with 300 parts of trichloromethane. The combined extracts are dried, filtered and evaporated, yielding 22 parts (100%) of 1,3-dihydro-1-[1-(3-piperidinyl)ethyl]-2H-benzimidazol-2-one as an oily residue.

EXAMPLE IV

To a stirred mixture of 43.5 parts of 1,3-dihydro-1-(1-methylethenyl)-2H-benzimidazol-2-one and 270 parts of N,N-dimethylformamide are added portionwise 10 parts of sodium hydride dispersion 60%. After stirring for 1 hour at about 40°–50° C., there are added 53 parts of 3-(chloromethyl)-1-(phenylmethyl)pyrrolidine and the whole is stirred and heated overnight at about 110° C. The reaction mixture is cooled and poured onto water. The product is extracted with 4-methyl-2-pentanone. The extract is dried, filtered and evaporated. The residue is purified by column-chromatography over silica gel using a mixture of trichloromethane and methanol (95:5 by volume) as eluent. The pure fractions are collected and the eluent is evaporated. The residue is taken up in a diluted hydrochloric acid solution and the whole is stirred for 1 hour at room temperature. After cooling, the mixture is alkalized and the product is extracted with 4-methyl-2-pentanone. The extract is dried, filtered and evaporated. The residue is triturated in 2,2'-oxybispropane with activated charcoal. The latter is filtered off and the filtrate is allowed to crystallize. The product is filtered off and dried, yielding 40 parts (53%) of 1,3-dihydro-1-[1-(phenylmethyl)-3-pyrrolidinylmethyl]-2H-benzimidazol-2-one.

A mixture of 40 parts of 1,3-dihydro-1-[1-(phenylmethyl)-3-pyrrolidinylmethyl]-2H-benzimidazol-2-one and 400 parts of methanol is hydrogenated at normal pressure and at room temperature with 5 parts of palladium-on-charcoal catalyst 5%. After the calculated amount of hydrogen is taken up, the catalyst is filtered off and the filtrate is evaporated. The residue is converted into the hydrochloride salt in 4-methyl-2-pentanone and 2-propanol. The salt is filtered off and dried, yielding 30 parts (96%) of 1,3-dihydro-1-(3-pyrrolidinylmethyl)-2H-benzimidazol-2-one monohydrochloride.

EXAMPLE V

A mixture of 25 parts of 1,3-dihydro-1-methyl-2H-benzimidazol-2-one, 64 parts of sodium methanolate solution 30% and 240 parts of methanol is stirred for one hour at room temperature. Then there are added 27.88 parts of 3-(chloromethyl)pyridine hydrochloride and stirring is continued for 3 hours at reflux temperature. The reaction mixture is cooled and the formed precipitate (sodium chloride) is filtered off. The filtrate is evaporated. The residue is crystallized from a mixture of 4-methyl-2-pentanone and 2,2'-oxybispropane. The product is filtered off and dried, yielding 16 parts (39.3%) of 1,3-dihydro-1-methyl-3-(3-pyridinylmethyl)-2H-benzimidazol-2-one; mp. 90° C.

A mixture of 16 parts of 1,3-dihydro-1-methyl-3-(3-pyridinylmethyl)-2H-benzimidazol-2-one and 200 parts of acetic acid is hydrogenated at normal pressure and at 50° C. with 2 parts of palladium-on-charcoal catalyst 10%. After the calculated amount of hydrogen is taken up, the catalyst is filtered off and the filtrate is evaporated. Water is added to the residue and the whole is alkalized with ammonium hydroxide. The product is extracted with methylbenzene. The extract is dried, filtered and evaporated, yielding 16.5 parts (100%) of 1,3-dihydro-1-methyl-3-(3-piperidinylmethyl)-2H-benzimidazol-2-one as an oily residue.

EXAMPLE VI

To a stirred mixture of 20 parts of 1-(2-hydroxy-5-methylphenyl)ethanone, 50.5 parts of (chloromethyl)oxirane and 40 parts of methanol are added dropwise 25 parts of sodium methoxide solution 30%. Upon completion, stirring is continued for 1 hour at room temperature. The reaction mixture is filtered and the filtrate is evaporated. The residue is dissolved in methylbenzene. The latter is washed with water, dried, filtered and evaporated. The residue is distilled, yielding 15 parts (55%) of 1-[5-methyl-2-(oxiranylmethoxy)phenyl]ethanone; bp. 140°–150° C. at 0.3 mm. pressure.

Following the same procedure and using equivalent amounts of respectively an appropriate phenol and an appropriate (halomethyl)oxirane there are also prepared:
  methyl 4-(oxiranylmethoxy)benzeneacetate as a residue;
  1-[5-fluoro-2-(oxiranylmethoxy)phenyl]ethanone; bp. 140° C. at 0.4 mm. pressure; and
  1-[5-bromo-2-(oxiranylmethoxy)phenyl]ethanone; bp. 162° C. at 0.4 mm. pressure.

EXAMPLE VII

A mixture of 3.6 parts of 2-(2-methoxyphenoxymethyl)oxirane, 5.3 parts of 1,3-dihydro-1-(3-piperidinylmethyl)-2H-benzimidazol-2-one monohydrochloride, 6 parts of sodium carbonate and 80 parts of ethanol is stirred and refluxed for 6 hours. The reaction mixture is cooled, filtered and evaporated. The residue is purified by column-chromatography over silica gel using a mixture of trichloromethane and methanol (90:10 by volume) as eluent. The pure fractions are collected and the eluent is evaporated. The residue is crystallized from a mixture of 4-methyl-2-pentanone and 2,2'-oxybispropane. The product is filtered off and recrystallized from 4-methyl-2-pentanone, yielding 1.8 parts (22%) of 1,3-dihydro-1-{1-[2-hydroxy-3-(2-methoxyphenoxy)propyl]-3-piperidinylmethyl}-2H-benzimidazol-2-one; mp. 158.1° C.

EXAMPLE VIII

Following the procedure of Example V and using equivalent amounts of the appropriate starting materials, the following compounds are prepared:

$$Ar-O-CH_2-\underset{\underset{OH}{|}}{CH}-CH_2-N\diagdown$$

| Ar | $R^2, R^3$ | Melting point in °C. |
|---|---|---|
| 4-Cl—$C_6H_4$ | H | 143.3 |
| 2-CN—$C_6H_4$ | H | 188.4 |
| 2-($C_2H_5O$)—$C_6H_4$ | H | 120.3 |
| 1-naphthalenyl | H | 141.2 |
| 2-Br—$C_6H_4$ | H | 165.2 |
| 2-($CH_2$=CH—$CH_2$)—$C_6H_4$ | H | 143.4 |
| 4-($CH_3CONH$)—$C_6H_4$ | H | 85.4 |
| 2-($CH_2$=CH—$CH_2$—O)—$C_6H_4$ | H | 108.7 |
| 2-naphthalenyl | H | 133.0 |
| 3,5-$(CH_3)_2$-4-Cl—$C_6H_2$ | H | 150.3 |
| 3-($CH_3CO$)—$C_6H_4$ | H | 116.1 |
| 2,3-$(CH_3)_2$—$C_6H_3$ | H | 176.5 |
| 2-($C_2H_5$)—$C_6H_4$ | H | 165.4 |
| 4-($C_6H_5$)—$C_6H_4$ | H | 151.1 |
| 4-CN—$C_6H_4$ | H | 195.5 |
| 2-($CH_3CO$)—$C_6H_4$ | H | 171.6 |
| 3-$CH_3$—$C_6H_4$ | H | 130.0 |
| 4-($CH_3CO$)—$C_6H_4$ | H | 137.0 |
| 4-($CH_3O$)—$C_6H_4$ | H | 121.3 |
| 4-$nC_3H_7$—$C_6H_4$ | H | 124.5 |
| 4-($nC_4H_9$—NH—CO—NH)—$C_6H_4$ | H | 150.1 |
| 4-i . $C_3H_7$—$C_6H_4$ | H | 120.3 |
| 2-(i . $C_3H_7$—O)—$C_6H_4$ | H | 119.8 |
| 4-$C_2H_5$—$C_6H_4$ | H | 111.3 |
| 4-F—$C_6H_4$ | H | 156.0 |
| 2-($CH_3CO$)-4-F—$C_6H_3$ | H | 161.5 |
| 2-($CH_3CO$)-4-Cl—$C_6H_3$ | H | 164.5 |
| 2-($CH_3CO$)-4-$CH_3$—$C_6H_3$ | H | 139.7 |
| 4-Br-2-($CH_3CO$)—$C_6H_3$ | H | 158.0 |
| 2-($CH_3CO$)-4-Cl—$C_6H_3$ | 6-Cl | 174.9 |
| 4-Br-2-($CH_3CO$)—$C_6H_3$ | 6-Cl | 177.7 |
| 2-($C_3H_7CO$)—$C_6H_4$ | 6-Cl | 171.9 |

EXAMPLE IX

A mixture of 4 parts of [(2-methoxyphenoxy)methyl]oxirane, 5.3 parts of 6-chloro-1,3-dihydro-1-(3-piperidinylmethyl)-2H-benzimidazol-2-one and 120 parts of 2-propanol is stirred and refluxed for 5 hours. The reaction mixture is cooled and evaporated. The residue is purified by column-chromatography over silica gel using a mixture of trichloromethane and methanol (90:10 by volume) as eluent. The pure fractions are collected and the eluent is evaporated. The residue is crystallized from 4-methyl-2-pentanone and 2,2'-oxybispropane. The product is filtered off and crystallized from 4-methyl-2-pentanone, yielding 2.5 parts (28%) of 6-chloro-1,3-dihydro-1-{1-[2-hydroxy-3-(2-methoxyphenoxy)propyl]-3-piperidinylmethyl}-2H-benzimidazol-2-one; mp. 167° C.

EXAMPLE X

Following the procedure of Example VII and using equivalent amounts of the appropriate starting materials, the following compounds are prepared:

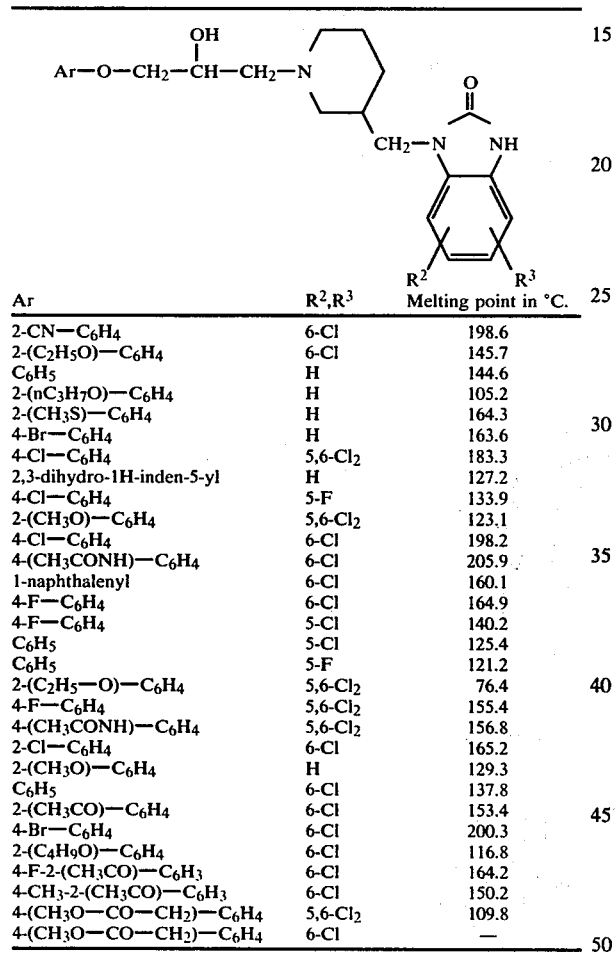

| Ar | R², R³ | Melting point in °C. |
|---|---|---|
| 2-CN—C₆H₄ | 6-Cl | 198.6 |
| 2-(C₂H₅O)—C₆H₄ | 6-Cl | 145.7 |
| C₆H₅ | H | 144.6 |
| 2-(nC₃H₇O)—C₆H₄ | H | 105.2 |
| 2-(CH₃S)—C₆H₄ | H | 164.3 |
| 4-Br—C₆H₄ | H | 163.6 |
| 4-Cl—C₆H₄ | 5,6-Cl₂ | 183.3 |
| 2,3-dihydro-1H-inden-5-yl | H | 127.2 |
| 4-Cl—C₆H₄ | 5-F | 133.9 |
| 2-(CH₃O)—C₆H₄ | 5,6-Cl₂ | 123.1 |
| 4-Cl—C₆H₄ | 6-Cl | 198.2 |
| 4-(CH₃CONH)—C₆H₄ | 6-Cl | 205.9 |
| 1-naphthalenyl | 6-Cl | 160.1 |
| 4-F—C₆H₄ | 6-Cl | 164.9 |
| 4-F—C₆H₄ | 5-Cl | 140.2 |
| C₆H₅ | 5-Cl | 125.4 |
| C₆H₅ | 5-F | 121.2 |
| 2-(C₂H₅—O)—C₆H₄ | 5,6-Cl₂ | 76.4 |
| 4-F—C₆H₄ | 5,6-Cl₂ | 155.4 |
| 4-(CH₃CONH)—C₆H₄ | 5,6-Cl₂ | 156.8 |
| 2-Cl—C₆H₄ | 6-Cl | 165.2 |
| 2-(CH₃O)—C₆H₄ | H | 129.3 |
| C₆H₅ | 6-Cl | 137.8 |
| 2-(CH₃CO)—C₆H₄ | 6-Cl | 153.4 |
| 4-Br—C₆H₄ | 6-Cl | 200.3 |
| 2-(C₄H₉O)—C₆H₄ | 6-Cl | 116.8 |
| 4-F-2-(CH₃CO)—C₆H₃ | 6-Cl | 164.2 |
| 4-CH₃-2-(CH₃CO)—C₆H₃ | 6-Cl | 150.2 |
| 4-(CH₃O—CO—CH₂)—C₆H₄ | 5,6-Cl₂ | 109.8 |
| 4-(CH₃O—CO—CH₂)—C₆H₄ | 6-Cl | — |

EXAMPLE XI

A mixture of 3.58 parts of (2-methoxyphenoxymethyl)oxirane, 4.4 parts of 1,3-dihydro-1-[1-(3-piperidinyl)ethyl]-2H-benzimidazol-2-one and 80 parts of 2-propanol is stirred and refluxed for 6 hours. The reaction mixture is evaporated. The residue is purified by column-chromatography over silica gel using a mixture of trichloromethane and methanol (96:4 by volume) as eluent. The pure fractions are collected and the eluent is evaporated. The residue is converted into the hydrochloride salt in 4-methyl-2-pentanone, 2,2'-oxybispropane and 2-propanol. The salt is filtered off and dried, yielding 1.5 parts (18%) of 1,3-dihydro-1-[1-{1-[2-hydroxy-3-(2-methoxyphenoxy)-propyl]-3-piperidinyl}ethyl]-2H-benzimidazol-2-one monohydrochloride; mp. 134° C.

EXAMPLE XII

A mixture of 4 parts of (4-chlorophenoxymethyl)oxirane, 5 parts of 1,3-dihydro-1-(3-pyrrolidinylmethyl)-2H-benzimidazol-2-one monohydrochloride, 6 parts of sodium carbonate and 80 parts of 2-propanol is stirred and refluxed for 5 hours. The reaction mixture is cooled, filtered and the filtrate is evaporated. The residue is crystallized from 4-methyl-2-pentanone, yielding 2.8 parts (35%) of 1-{1-[3-(4-chlorophenoxy)-2-hydroxypropyl]-3-pyrrolidinylmethyl}-1,3-dihydro-2H-benzimidazol-2-one; mp. 129° C.

EXAMPLE XIII

Following the procedure of Example X and using equivalent amounts of the appropriate starting materials there are prepared:

1,3-dihydro-1-{1-[2-hydroxy-3-(2-methoxyphenoxy)-propyl]-3-pyrrolidinylmethyl}-2H-benzimidazol-2-one; mp. 111.2° C.; and 1,3-dihydro-1-[1-(2-hydroxy-3-phenoxypropyl)-3-pyrrolidinylmethyl]-2H-benzimidazol-2-one; mp. 126.6° C.

EXAMPLE XIV

A mixture of 7.5 parts of 2,3-dihydro-2-oxiranyl-1,4-benzodioxine, 5.3 parts of 1,3-dihydro-1-(3-piperidinylmethyl)-2H-benzimidazol-2-one monohydrochloride, 6 parts of sodium carbonate and 80 parts of ethanol is stirred and refluxed for 5 hours. The reaction mixture is cooled, filtered and the filtrate is evaporated. The residue is purified by column-chromatography over silica gel using a mixture of trichloromethane and methanol (95:5 by volume) as eluent. The pure fractions are collected and the eluent is evaporated. The residue is crystallized from a mixture of 4-methyl-2-pentanone and 2,2'-oxybispropane. The product is filtered off and dried, yielding 1 part (11%) of 1-{1-[2-(2,3-dihydro-1,4-benzodioxin-2-yl)-2-hydroxyethyl]-3-piperidinylmethyl}-1,3-dihydro-2H-benzimidazol-2-one; mp. 154° C.

EXAMPLE XV

A mixture of 11 parts of methyl 4-{3-[3-(5,6-dichloro-2,3-dihydro-2-oxo-1H-benzimidazol-1-ylmethyl)-1-piperidinyl]-2-hydroxypropoxy}benzeneacetate and 800 parts of methanol saturated with ammonia is stirred and heated in an autoclave at 110° C. and at a pressure of 85.7 lbs/sq. inch. The reaction mixture is cooled and evaporated. The residue is stirred in 4-methyl-2-pentanone. The product is filtered off and purified by column-chromatography over silica gel using a mixture of trichloromethane and methanol (90:10 by volume) as eluent. The pure fractions are collected and the eluent is evaporated. The residue is crystallized from 4-methyl-2-pentanone and a small amount of 2-propanol. The product is filtered off and dried, yielding 2.7 parts (25%) of 4-{3-[3-(5,6-dichloro-2,3-dihydro-2-oxo-1H-benzimidazol-1-ylmethyl)-1-piperidinyl]-2-hydroxypropoxy}benzeneacetamide; mp. 147.9° C.

Following the same procedure there is also prepared: 4-{3-[3-(6-chloro-2,3-dihydro-2-oxo-1H-benzimidazol-1-ylmethyl)-1-piperidinyl]-2-hydroxypropoxy}benzeneacetamide; mp. 183°-188° C.

What is claimed is:
1. A chemical compound selected from the group consisting of a 1,3-dihydro-2H-benzimidazol-2-one derivative having the formula

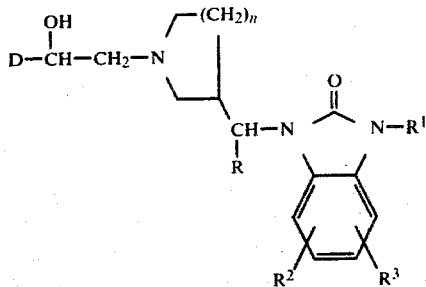

and the therapeutically acceptable acid addition salts thereof;
wherein:
D is a member selected from the group consisting of the radicals Ar—X—CH$_2$— and

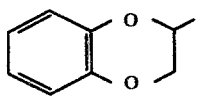

wherein X is selected from the group consisting of O and S and Ar is selected from the group consisting of phenyl, substituted phenyl, naphthalenyl and 2,3-dihydro-1H-indenyl, wherein substituted phenyl is phenyl having from 1 to 3 substituents each independently selected from the group consisting of halo, lower alkyl, lower alkenyl, lower alkynyl, lower alkyloxy, lower alkenyloxy, lower alkynyloxy, lower alkyloxy-lower alkyloxy, phenyl, cyano, lower alkanoyl, benzoyl, nitro, amino, lower alkanoylamino, mono- and di(lower alkyl)amino, aminocarbonylamino, phenylaminocarbonylamino, mono- and di(lower alkyl)aminocarbonylamino, lower alkylthio, phenyllower alkyl, 3-phenyl-2-propen-1-yloxy, aminocarbonyllower alkyl, mono- and di(lower alkyl)aminocarbonyllower alkyl and lower alkyloxycarbonyllower alkyl, provided that when more than 1 substituent is present only one thereof may be selected from the group consisting of phenyl, phenyllower alkyl, benzoyl, aminocarbonylamino, phenylaminocarbonylamino, mono- and di(lower alkyl)aminocarbonylamino, aminocarbonyllower alkyl, mono- and di(lower alkyl)aminocarbonyllower alkyl, lower alkyloxycarbonyllower alkyl, amino, nitro and cyano;

R is selected from the group consisting of hydrogen and lower alkyl; n is the integer 1 or 2, provided that when said R is lower alkyl then said n is 2;

R$^1$ is a member selected from the group consisting of hydrogen, lower alkyl, lower alkenyl, lower alkyloxy-lower alkyl, phenoxylower alkyl, lower alkylcarbonyl-lower alkyl, cyano-lower alkyl, phenyl-lower alkyl, hydroxy-lower alkyl, di(lower alkyl)aminolower alkyl, 1-pyrrolidinyl-lower alkyl, 1-piperidinyl-lower alkyl and lower alkyloxycarbonyl-lower alkyl; and R$^2$ and R$^3$ are each independently selected from the group consisting of hydrogen, halo, lower alkyl, lower alkyloxy and trifluoromethyl.

2. A chemical compound selected from the group consisting of 2-{3-[3-(6-chloro-2,3-dihydro-2-oxo-1H-benzimidazol-1-yl-methyl)piperidinyl]-2-hydroxypropoxy}benzonitrile and the therapeutically acceptable acid addition salts thereof.

3. A chemical compound selected from the group consisting of 1-{1-[3-(2,3-dimethylphenoxy)-2-hydroxypropyl]-3-piperidinylmethyl}-1,3-dihydro-2H-benzimidazol-2-one and the therapeutically acceptable acid addition salts thereof.

4. A chemical compound selected from the group consisting of 5,6-dichloro-1-{1-[3-(2-ethoxyphenoxy)-2-hydroxypropyl]-3-piperidinylmethyl}-1,3-dihydro-2H-benzimidazol-2-one and the therapeutically acceptable acid addition salts thereof.

5. A chemical compound selected from the group consisting of 6-chloro-1,3-dihydro-1-{1-[2-hydroxy-3-(2-methoxyphenoxy)-propyl]-3-piperidinylmethyl}-2H-benzimidazol-2-one and the therapeutically acceptable acid addition salts thereof.

6. A chemical compound selected from the group consisting of 1-{1-[3-(4-bromophenoxy)-2-hydroxypropyl]-3-piperidinylmethyl}-1,3-dihydro-2H-benzimidazol-2-one and the therapeutically acceptable acid addition salts thereof.

7. A chemical compound selected from the group consisting of 1-{1-[3-(2-bromophenoxy)-2-hydroxypropyl]-3-piperidinyl-methyl}-1,3-dihydro-2H-benzimidazol-2-one and the therapeutically acceptable acid addition salts thereof.

8. A chemical compound selected from the group consisting of 1-{1-[3-(4-chloro-3,5-dimethylphenoxy)-2-hydroxypropyl]-3-piperidinylmethyl}-1,3-dihydro-2H-benzimidazol-2-one and the therapeutically acceptable acid addition salts thereof.

* * * * *